United States Patent [19]

Potts

[11] 4,062,954

[45] Dec. 13, 1977

[54] PROCESS FOR USING A STEROID COMPOUND

[75] Inventor: Gordon Oliver Potts, Chatham, N.Y.

[73] Assignee: Sterling Drug Inc., New York, N.Y.

[21] Appl. No.: 753,989

[22] Filed: Dec. 27, 1976

[51] Int. Cl.$^2$ ............................................. A61K 31/58
[52] U.S. Cl. ............................ 424/241; 260/239.55 R
[58] Field of Search ................... 424/241; 260/239.55

[56] References Cited

U.S. PATENT DOCUMENTS 3,296,255   1/1967   Clifton et al. .................. 260/239.55

*Primary Examiner*—Elbert L. Roberts
*Attorney, Agent, or Firm*—Thomas L. Johnson; B. Woodrow Wyatt

[57] ABSTRACT

The compound 2α-cyano-4α,5α-epoxyandrostan-17β-ol-3-one and its esters are useful in disrupting pregnancy in female mammals upon oral administration.

2 Claims, No Drawings

PROCESS FOR USING A STEROID COMPOUND

BACKGROUND OF THE INVENTION

1. Field of the Invention

This invention relates to a method of disrupting pregnancy in female mammals by administering a steroid having abortifacient activity.

2. Description of the Prior Art

Clinton and Manson U.S. Pat. No. 3,296,255, issued Jan. 3, 1967, discloses a series of 2-cyano-3-oxo steroids. The compounds are there stated to possess endocrinological and pharmacological activity, for example, adrenal inhibiting, pituitary inhibiting, electrolyte modifying, hypotensive and coronary dilator properties.

A specific compound disclosed in Example 16(b) of U.S. Pat. No. 3,296,255 is 2α-cyano-4α, 5α-epoxyandrostan-17β-ol-3-one having the formula

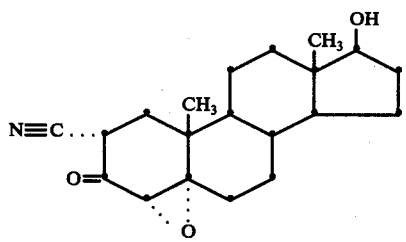

Compound I possesses adrenal cortical inhibitory activity [Neumann et al., Journal of Medicinal Chemistry 13, 948 (1970)].

Potts U.S. Pat. No. 3,966,926, issued June 29, 1976, discloses a method for disrupting pregnancy in a female mammal by oral administration of 17β-hydroxy-4,4,17α-trimethylandrost-5-eno[2,3-d]isoxazole or a pharmaceutically acceptable ester thereof.

SUMMARY OF THE INVENTION

This invention relates to a method for disrupting pregnancy in a female mammal which comprises administering orally to said mammal, subsequent to implantation of a fertilized ovum in said mammal, an abortifaciently effective amount of 2α-cyano-4α,5α-epoxyandrostan-17β-ol-3-one or a pharmaceutically acceptable ester thereof.

DETAILED DESCRIPTION INCLUSIVE OF PREFERRED EMBODIMENTS

2α-Cyano-4α,5α-epoxyandrostan-17β-ol-3-one (Compound I) blocks the conversion of pregnenolone to progesterone, and thus inhibits the formation of ovarian or placental progesterone necessary for the maintenance of pregnancy. Compound I is thus effective as an abortifacient at a time immediately after implantation of the fertilized ovum and at any time during the pregnancy while progesterone is essential for maintenance of the pregnancy.

Compound I or an ester thereof is preferably administered in a daily dose of between 25 and 500 mg/kg of body weight for a period of between 1 and 5 days; and preferably at a time at least about 8 days after exposure to insemination.

The abortifacient activity of Compound I was established by the following laboratory studies and data obtained thereby.

a. Testing in rats

Male and female rats of the Spargue Dawley strain were used. Following an overnight mating exposure, vaginal smears were taken and insemination was determined. The day spermatozoa were found was designated day 1 of pregnancy. Compound I as a suspension in 1 percent gum tragacanth (w/v) was administered orally in a volume of 10 ml per kg once on day 10 of pregnancy. On the fifteenth day of pregnancy, the rats were killed with an overdose of pentobarbital sodium and the number of uterine implantation sites was determined. Each implantation site was judged to be a developing fetus, a dead fetus or a resorption site. Only those rats which had at least one developing fetus were considered pregnant.

The results are given in the following Table I:

TABLE I

| | Compound I (mg/kg) | | | | | |
|---|---|---|---|---|---|---|
| | 0 | 62.5 | 125 | 250 | 500 | 1000 |
| Body Weight | | | | | | |
| Initial | 230 | 229 | 229 | 229 | 230 | 229 |
| Final | 291 | 287 | 274 | 273 | 270 | 266 |
| Treated Females | | | | | | |
| Total Number | 7 | 7 | 7 | 7 | 7 | 7 |
| No. Pregnant | 7 | 6 | 5 | 1 | 0 | 0 |
| Pregnancy Rate (%) | 100 | 86 | 71 | 14 | 0 | 0 |
| Pregnancy Data | | | | | | |
| Ave. No./Pregnant Rat | | | | | | |
| Implantation Sites | 12.9 | 14.3 | 13.4 | 14 | — | — |
| Resorption Sites | 0.7 | 0.8 | 4.0 | 1 | — | — |
| Fetuses | 12.2 | 13.5 | 9.4 | 13 | — | — |
| Percent Developing Fetuses | 100 | 100 | 100 | 100 | — | — |

Compound I was effective in disrupting pregnancy in the rat when administered once on day 10 of pregnancy. The results in Table I show that no fetuses survived when the drug was administered at a dose of 500 mg per kg on that single day. One of 7 rats had an apparently normal pregnancy following treatment with a dose of 250 mg per kg. At a dose of 125 mg per kg, there was a modest increase in the number of resorption sites although 5 of 7 rats had developing fetuses. Lower doses had no effect on the pregnancy rate or on the number of developing fetuses.

b. Testing in monkeys

The oral abortifacient activity of Compound I in the rhesus monkey (Macaca mulatta) was evaluated as early as pregnancy could be determined in our laboratory using the bioassay of chorionic gonadotrophin. The monkeys were approximately 24 to 28 days pregnant when treatment began. Compound I as a suspension in 1 percent gum tragacanth (w/v) was administered orally in a volume of 20 ml per monkey per day for 5 days and the progress of the pregnancy was assessed by bimanual palpation of the uterus and the return of regular menstrual cycles.

The results are given in the following Table II:

TABLE II

| Compound I mg/monkey/day × 5 | No. of Monkeys | No. of Monkeys that Aborted |
| --- | --- | --- |
| 100 | 5 | 0 |
| 250 | 4 | 2 |
| 500 | 4 | 4 |
| 1000 | 9 | 9 |

The results in Table II show that Compound I is an orally effective abortifacient agent in the monkey. When administered for 5 days beginning immediately following a positive pregnancy test, abortions occurred in 13 monkeys treated with this drug at a dose of 500 mg or more per monkey per day. At a dose of 250 mg per day, abortions occurred in 2 of 4 monkeys while abortion did not occur in the 5 monkeys treated with 100 mg per day.

c. Testing in rabbits

Compound I was administered to pregnant rabbits at daily oral doses of 5.0, 25.0, 75.0 and 125.0 mg/kg during days 6–18 of gestation. Doses of 75.0 and 125.0 mg/kg completely interrupted pregnancy. Interruption of pregnancy occurred very early during gestation in the 75.0 and 125.0 mg/kg groups and there were no fetuses from these groups. Fetuses from the 5.0 and 25.0 mg/kg groups were normal. The 25.0 mg/kg dose decreased the number of expected litters by approximately 50%.

Compound I can also be used in the form of a pharmaceutically acceptable ester thereof wherein the 17-hydroxy group is esterified with a carboxylic acid. The carboxylic acid moiety preferably has from one to about ten carbon atoms and a molecular weight less than about 200, of the types described in U.S. Pat. No. 3,296,255. The esters are prepared by conventional esterification procedures, starting from Compound I, or by selective hydrolysis of the esterified 4α,5α-epoxyandrostano-[2,3-d]isoxazole intermediate. Exemplary of such esters are 4α,5α-epoxyandrostan-17β-ol-3-one acetate [m.p. 194.8°–198.0° C., $[\alpha]_D^{25}$ = +116.2° (1% in pyridine)] and hemisuccinate [m.p. 145°–150° C., $[\alpha]_D^{25}$ = −14.3° (1% in chloroform)].

2α-Cyano-4α,5α-epoxyandrostan-17β-ol-3-one (Compound I) or a pharmaceutically acceptable ester thereof is prepared for use by incorporating it in an inert pharmaceutical carrier. The formulation is prepared by dissolving or suspending the steroid in a pharmaceutically acceptable liquid vehicle, e.g. aqueous ethanol, glycol, cottonseed oil solution or oil-water emulsion, gum tragacanth suspension, or the like; or by incorporating the steroid in unit dosage form as tablets or capsules either alone or in combination with conventional adjuvants, e.g. calcium carbonate, starch, lactose, talc, magnesium stearate, gum acacia, and the like. Illustrative capsule mix formulations are as follows:

|  | mg/capsule | mg/capsule |
| --- | --- | --- |
| Compound I* (micronized) | 100 | 200 |
| Starch | 62 | 76.6 |
| Lactose | 62 | 76.6 |
| Talc | 5 | 5 |
| Magnesium stearate | 1 | 1.8 |
| Net Weight | 230 | 360 |

*2α-Cyano-4α,5α-epoxyandrostan-17β-ol-3-one

I claim:

1. A method for disrupting pregnancy in a female mammal which comprises administering orally to said mammal, subsequent to implantation of a fertilized ovum in said mammal, an abortifaciently effective amount of 2α-cyano-4α,5α-epoxyandrostan-17β-ol-3-one or a pharmaceutically acceptable ester thereof.

2. A method according to claim 1 in which 2α-cyano-4α,5α-epoxyandrostan-17β-ol-3-one is administered in a daily dose of between 25 and 500 mg/kg of body weight for a period of between 1 and 5 days.

* * * * *